US007869637B2

(12) United States Patent
Baumgart et al.

(10) Patent No.: US 7,869,637 B2
(45) Date of Patent: Jan. 11, 2011

(54) HISTOGRAM CALCULATION FOR AUTO-WINDOWING OF COLLIMATED X-RAY IMAGE

(75) Inventors: John Baumgart, Hoffman Estates, IL (US); Gerhard Litz, Lonnerstadt (DE)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1105 days.

(21) Appl. No.: 11/555,754

(22) Filed: Nov. 2, 2006

(65) Prior Publication Data
US 2008/0025586 A1 Jan. 31, 2008

Related U.S. Application Data

(60) Provisional application No. 60/834,447, filed on Jul. 31, 2006.

(51) Int. Cl.
*G06K 9/00* (2006.01)
*G06K 9/32* (2006.01)
*G06K 9/40* (2006.01)
(52) U.S. Cl. .................. 382/128; 382/260; 382/299
(58) Field of Classification Search ......... 382/128–132, 382/199, 260, 299
See application file for complete search history.

(56) References Cited

U.S. PATENT DOCUMENTS

| | | | | |
|---|---|---|---|---|
| 4,503,844 | A | * | 3/1985 | Siczek ..................... 606/245 |
| 5,369,678 | A | | 11/1994 | Chiu et al. |
| 6,055,295 | A | | 4/2000 | Murthy et al. |
| 6,106,152 | A | * | 8/2000 | Thunberg ................. 378/205 |
| 6,377,656 | B1 | | 4/2002 | Ueki et al. |
| 6,614,877 | B2 | | 9/2003 | Anderton |
| 6,734,880 | B2 | * | 5/2004 | Chang et al. .............. 715/738 |
| 6,895,077 | B2 | | 5/2005 | Karellas et al. |
| 7,116,752 | B2 | | 10/2006 | Takahashi et al. |
| 2003/0095627 | A1 | * | 5/2003 | Anderton ................. 378/98.7 |
| 2003/0161518 | A1 | * | 8/2003 | Vuylsteke ................ 382/128 |
| 2004/0009459 | A1 | * | 1/2004 | Anderson et al. .......... 434/262 |
| 2006/0269111 | A1 | * | 11/2006 | Stoecker et al. .......... 382/128 |
| 2007/0189591 | A1 | * | 8/2007 | Lu et al. .................. 382/128 |
| 2008/0219540 | A1 | * | 9/2008 | Ter Mors ................. 382/132 |

* cited by examiner

*Primary Examiner*—Vu Le
*Assistant Examiner*—Amara Abdi
(74) *Attorney, Agent, or Firm*—Alexander J Burke

(57) ABSTRACT

An X-ray diagnostic imaging system is disclosed that includes an X-ray source for controlling an X-ray beam radiated towards a patient under examination. The X-ray source includes an X-ray tube and X-ray collimator assembly. The system includes an-ray imaging device arranged for receiving the X-ray beam after is has passed through the patient to acquire latent image frames of a region of interest (ROI) of the patient's anatomy, and a system controller coupled to X-ray source and X-ray imaging device for controlling latent image frame acquisition and post-acquisition processing. The controlling includes controlling the X-ray imaging device and X-ray positioning, and collimator assembly operation. An image processing chain including an image processor coupled to the system controller, receives latent image frames from the X-ray imaging device for processing, including calculating a histogram from which pixels within a collimated area are removed. The improved histogram is used in post-acquisition processing such as a window level setting. An X-ray image processed by functions using the improved histogram is displayed by a display device coupled to the image processing chain.

19 Claims, 5 Drawing Sheets

HISTOGRAM CALCULATION FOR AUTO-WINDOWING OF COLLIMATED X-RAY IMAGE

PRIORITY CLAIM TO RELATED APPLICATION

This application claims priority from U.S. Provisional Patent Application Ser. No. 60/834,447, filed Jul. 31, 2006, the disclosure of which is incorporated by reference in its entirety herein.

BACKGROUND OF THE INVENTION

1. Field of the Invention

The present invention relates to medical X-ray imaging, and more particularly relates to collimator sensitive histogram generation for use in the automatic adjustment of window level settings in medical X-ray imaging.

2. Description of the Related Art

Conventional X-ray imaging systems for digital radiography are used for various imaging applications including without limitation anatomical background imaging and angiographic imaging to highlight a patient's vasculature using such techniques as digital subtraction angiography (DSA) and live fluoroscopy roadmapping. X-ray imaging systems include an X-ray source and X-ray capture device such as a digital flat panel detector to convert the X-ray energy striking the detector into a latent image frame. That is, the X-ray beam or radiation strikes a CCD or flat panel detector, where the captured radiation image is converted into a digital signal, comprising rows and columns of pixels. The X-ray beam is adjusted and shaped to facilitate image acquisition, whereafter the digital signal data are manipulated to better visualize the image produced.

X-ray imaging systems may include various displays, panels, consoles, workstations, etc., with user interfaces such as keyboards, switches, dials, trackballs, joysticks, etc., that enable an operator to control operations such as image contrast, brightness, image blur and noise in the produced image. X-ray systems include various mechanisms for preventing direct exposure from the X-ray beam as well as from scattered X-rays from reaching the flat panel detector. The mechanisms also include X-ray collimators or beam-limiting devices, which adjust the shape of the radiated X-ray beam to an extent necessary for imaging patient anatomy within a desired field of view (FOV). For example, a collimator may be adjusted during the examination for each image taken to optimally cover or mask part of the X-ray beam FOV in which no body part, or non-relevant body parts are located, i.e., outside the FOV. Because manually setting the collimator, for example, at each station used to carry out an angiographic study of leg vasculature for a mask run, and saving the settings for actual image acquisition is cumbersome and time consuming, automatic collimator adjustment functions have been developed. U.S. Pat. No. 6,055,295, commonly owned, discloses a system and method for automatically setting the collimator of an X-ray imaging system at the time of image acquisition.

As mentioned, the raw image data striking the detector is arranged in and transferred from the detector in a form of pixels. Pixels may have digital intensity values limited by the system contrast ability and the digital size of the pixel. For example, a 12-bit pixel may have a value from 0 to 4095. A look-up table (LUT) is used to map pixel values to one of the shades of grey in the displayed image. The digital image comprising a frame or set of pixels is processed by mapping the digital gray values into specific densities or luminances for a specified display means, e.g., a CRT display. Difficulties arise, however, in attempting to display the full acquisition dynamic range, such as the aforementioned image blackening found in film-based systems. Collimators may be used to block (by limiting the X-ray beam) the area outside the FOV. This process normally results in black borders comprising the shielded pixels surrounding the field in the viewed image. Radio-opaque elements and substances such as a contrast medium used in angiographic applications also appear black in an acquired image frame. Without background removal, background may affect post-acquisition processing and decrease contrast levels and therefore image quality.

Techniques such as window width (contrast), window level adjusting (brightness) and edge enhancement (unsharp masking), and background removal have developed to improve image display. Background removal processes improve contrast in the displayed image. Window level adjustment processes may be controlled manually at a workstation or automatically in an imaging chain background process to improve viewed image quality. U.S. Pat. No. 6,106,152, commonly owned, discloses an X-ray imaging system with an X-ray source that includes an X-ray tube and collimator to limit or adjust the radiated X-ray beams. A test exposure may be acquired with the system to adjust the collimators or position the X-ray beams in relation to a digital detector, such as a flat panel detector, focusing the FOV. An image of the outer contours of the patient may be obtained and processed to have sufficient contrast for viewing on a display.

Processing shifts of the upper or lower edge of the acquired image gray-scale level changes the window range, carried out by first determining a minimum and maximum of a global image histogram, automatically, or based on manual inputs to adjust a windowed image. A histogram is a gray scale value distribution showing the frequency of occurrence of each gray level value in the image. U.S. Pat. No. 6,127,669 discloses window and level control based on histogram analysis. In such histogram based level adjustment systems and processes, the minimum and maximum levels within the histogram define the window range, e.g., their average value. Conventionally, the window range and window level are used to generate the default look-up table, or LUT. Background removal is based on an assumption that the gray-scale values of foreground (anatomical structure in the field of view) and background (outside patient boundary) are distinguishable by use of the histogram.

Pixels outside the exposed viewing area can cause histograms used for the automatic window adjustment to be skewed, resulting in incorrect image display because known histograms are computed over the entire image. Accordingly, known histogram calculations attempt to exclude acquired image pixels that are presumed to be in the raw image areas under the collimator. That is, conventional histogram calculations are based on a presumption that those pixels of collimated image areas contain the darkest pixels of the image. Preconfigured numbers of pixels are therefore excluded from the low and high ends of the histogram before window level settings are calculated. But where the collimator area is significant, or if there is image processing in the imaging chain before histogram calculation such that the collimated area is not the darkest area of the image, or if the pixels under the collimator are undefined by the data source, the histogram becomes skewed, affecting image quality.

It would be desirable, therefore, to the skilled artisan and clinician alike to have use of a system and method that overcomes the shortcomings of prior art histogram calculation and modification, excludes pixels known to be under a collimated area from the histogram calculations, particularly in angiographic imaging. To that end, the present invention provides a system and method that overcomes the shortcomings of prior art histogram calculation and modification, which excludes pixels known to be under a collimated area from the histogram for use in various processes, including window level calculations.

SUMMARY OF THE INVENTION

To that end, the invention includes an X-ray diagnostic imaging system that carries out histogram calculation for automatic image adjustment that excludes any pixels from the histogram calculation that are located under a collimated detector area, for improved image processing. The system includes an X-ray source for controlling an X-ray beam radiated towards a patient under examination, and the X-ray source comprises an X-ray tube and X-ray collimator assembly. An X-ray imaging device or detector is arranged for receiving the X-ray beam after it has passed through the patient to acquire latent image frames of a region of interest (ROI) of the patient's anatomy. A system controller is coupled to the X-ray source and the X-ray imaging device for controlling latent image frame acquisition and post-acquisition processing, including controlling X-ray tube and X-ray imaging device positioning, and collimator assembly adjustment. An image processing chain comprising an image processor and coupled to the system controller receives latent image frames from the X-ray imaging device for processing, and calculates the histogram that includes excluding pixels known to be background, for example, those pixels known to be under a collimated area. A display device coupled to the image processing chain displays post-processed image frames as an X-ray diagnostic image of the ROI with improved contrast.

The image processing chain forms the X-ray diagnostic image for display to include a first background border representative of rendered electronic shutter. The border may represent background pixels excluded from the novel histogram calculation. The border is presented in the displayed image proximate to or surrounding the ROI, and is readily distinguishable from the ROI. Preferably, a second background border between the first background border and the ROI is displayed representing pixels within the latent image frames within a collimator masked area. These pixels comprising collimated-area pixels in the second background border are also excluded from the novel histogram calculation function. The histograms calculated without including collimated area pixels and/or background pixels provide for improved statistical-based processing, including window level adjusting.

The invention also includes a method for X-ray diagnostic imaging with steps of projecting an X-ray beam towards a patient under examination while limiting a shape of the X-ray beam using collimation or other beam limiting to shape and focus the beam FOV in order to acquire image information of a particular region of interest (ROI) within the patient's anatomy. The shaped beam is captured after it has passed through the patient to acquire a stream of latent image frames, and the latent image frames are processed in an image chain background process. The processing includes implementing a background removal process to remove pixels that fall outside the ROI, particularly those from the collimated areas, and calculating a histogram for the image without using the removed pixels. Various post-acquisition processing, such as calculating window level settings, use the novel histogram to generate an improved X-ray image. The viewed image is arranged so that it includes not only the ROI, but an image border representative of collimation, and backgrounds (clearly identified).

DESCRIPTION OF DRAWING FIGURES

An understanding of the present invention can be gained from the following detailed description of embodiments of the invention, taken in conjunction with the accompanying drawings of which:

DETAILED DESCRIPTION OF EXEMPLARY EMBODIMENTS

Figure 1:
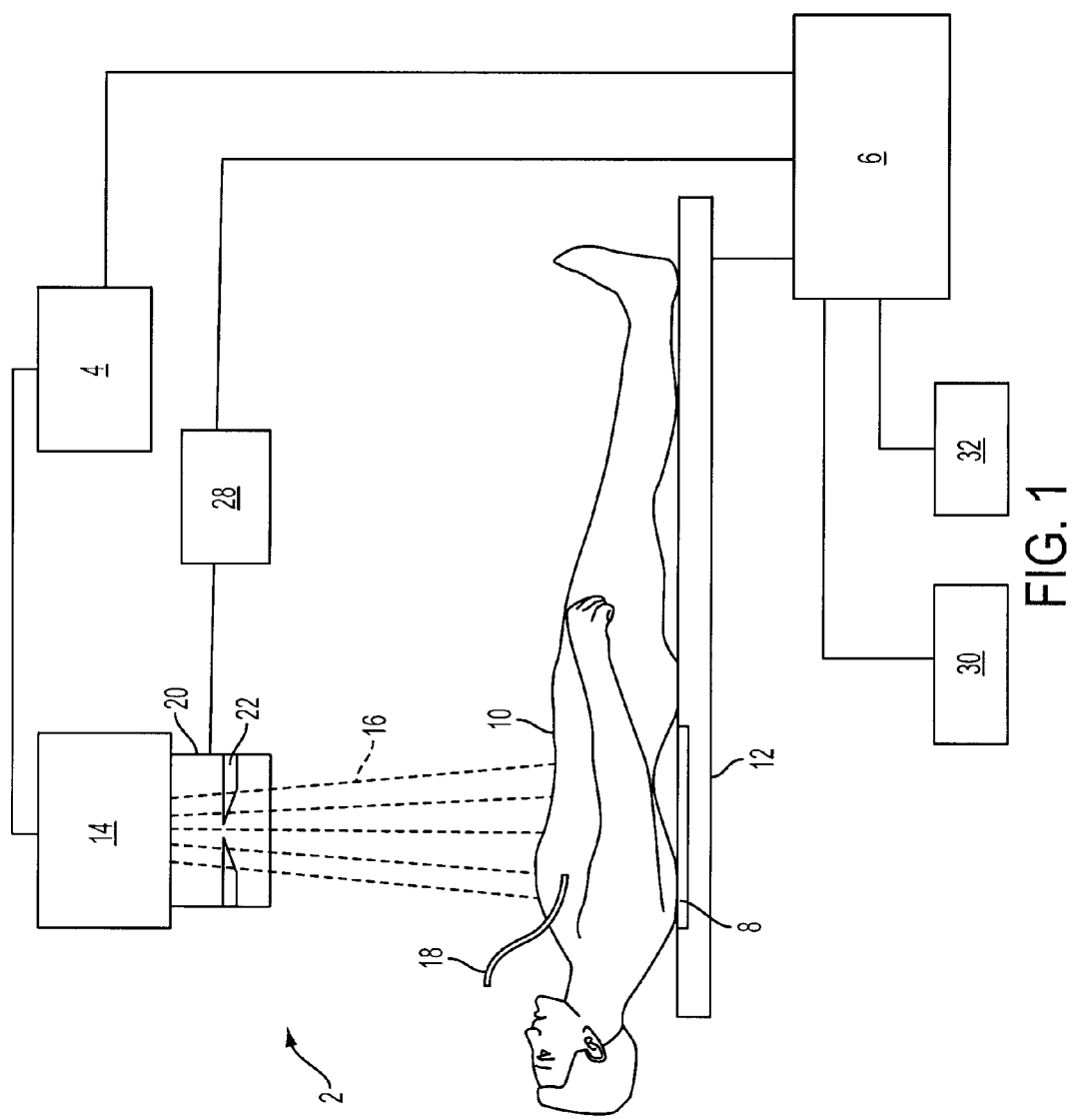
FIG. 1 is a schematic representation of an X-ray diagnostic imaging system constructed to implement an exemplary histogram-based processing in accordance with an embodiment of the invention.

Reference will now be made in detail to embodiments of the present invention, examples of which are illustrated in the accompanying drawings, wherein like reference numerals refer to like elements throughout.

FIG. 1 represents an X-ray diagnostic imaging system 2 in accordance with an embodiment of the invention, under which is a patient 10 undergoing an X-ray fluoroscopic procedure. The X-ray system 2 is constructed to calculate a novel and improved histogram to support various post-acquisition processing such as window level setting, wherein pixels not included in the desired ROI, such as pixels located in collimated areas, and background pixels, are excluded from the histogram calculation. X-ray system 2 includes a high voltage transformer assembly 4, an X-ray source 14 with an X-ray tube, and a collimator assembly 20 including beam limiting filter plates 22. X-ray source 14 emits X-ray radiation 16 during a diagnostic or interventional procedure that is limited by the collimator assembly 20 before it passes through the patient 10 striking a detector 8. The detector may be set in a patient table 12. It should be noted that the figure is included for exemplary purposes only. The detector may be under the table or on a stand where the system allows for standing X-ray examination, but the arrangement does not limit the invention to any one embodiment. X-ray detectors are generally flat panel detectors comprising semiconductor devices, but may comprise an image intensifier and optical system. The detector 8 detects X-ray transmission data acquired as the X-ray beam 16 passes through the patient 10, and outputs the acquired frames to an image control and processing sub-system 6.

The an image control and processing sub-system 6 receives the acquired image data for processing, and will typically include a detector interface, memory, X-ray beam limiting interface, high voltage transformer assembly interface, image processor or CPU, image condition storage means, and a video signal converting means. The image control and processing sub-system 6 is electrically connected to a control console 30 or work station, including user input devices, and a display or monitor 32. The user input device is included to allow some user control of the image acquisition and display process. The sub-system 6 is coupled to a position-detecting device 28 and a high voltage transformer assembly 4. The position-detecting device 28 is connected to collimator assembly 20, and detects positional information related to the beam limiting by the X-ray collimator assembly 20, providing the information to the processor inside the image control and processing sub-system 6. The collimator assembly 20 detects a size of a region upon which the beam limiting filter plates 22 shape X-ray radiation 16, and a distance between the plates 22 to the detector 8, etc. The physical information is provided to the control and processing system 6 to control the field of view (FOV) at the patient to achieve an image with a desired ROI. The collimation information is used for calculating the novel histogram described herein, and may be used for automatic contrast control. Accordingly, collimator blocked pixels are excluded from histogram generated for improved post-acquisition processing using the histogram.

A common application of X-ray systems such as X-ray system 2 is monitoring a location of a catheter 18 inside the patient 10. Such catheters may be used for balloon angioplasty, laser ablation or like procedures, now often used in place of traditional invasive surgery. While FIG. 1 shows the catheter 18 inside patient 10, the X-ray diagnostic imaging system 2 may be used for other purposes, such as a guide wire, needle, tube detection, and non-interventional imaging procedures. For a more detailed understanding of using X-ray diagnostic imaging systems for tracking catheters and the like during an interventional procedure, the reader is directed to commonly owned U.S. Pat. No. 5,369,678, and U.S. Pat. No. 7,116,752 which are incorporated herein by reference and which discuss X-ray beam limiting in detail, including brightness control.

Figure 2:
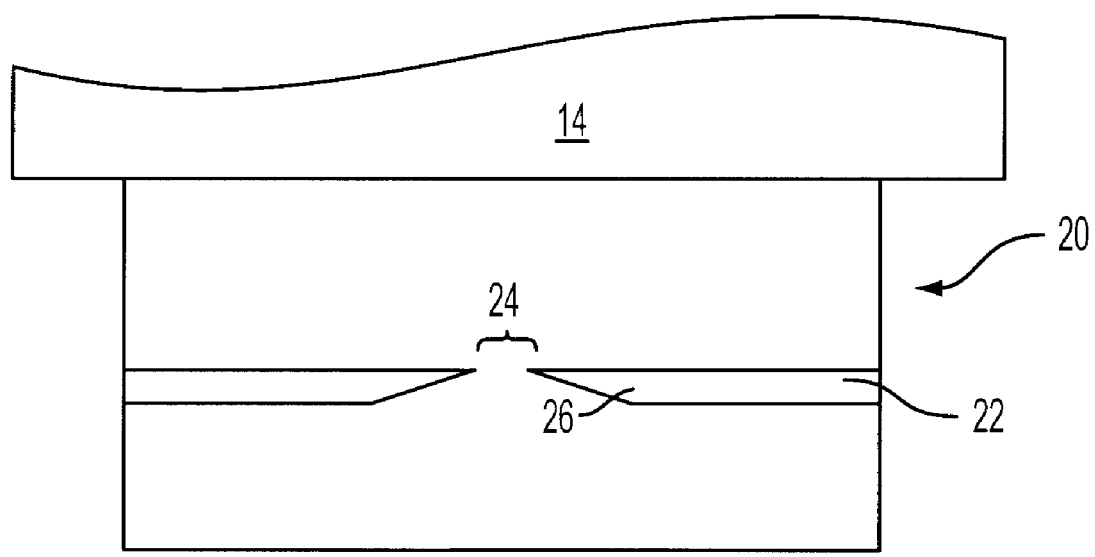
FIG. 2 is schematic diagram of an exemplary collimator assembly that may be included in the X-ray diagnostic imaging apparatus in accordance with an embodiment of the invention.

An enlarged view of collimator assembly 20 is shown in FIG. 2. Beam limiting filter plates 22 are shown therein to include a tapered region 26 surrounding a central aperture 24 for passing a portion of X-ray radiation 16 into the patient 10. Although one aperture 24 is shown in FIG. 2, a plurality of apertures may be formed in a close pattern so that the X-ray radiation passing through each of the apertures will overlap in a substantially common region. In addition, the thickness of the filter plates 24 may be constructed to change from a maximum value distal from the central aperture 24, to a minimum value bordering the aperture. The filter plates are typically made of a material that is semi-transparent to the X-ray radiation 16. Histogram generation is carried out in a background imaging chain using only those captured pixels in the ROI, with the background and collimator area pixels removed prior to histogram calculation. That is, the histogram is calculated after collimator and shutter blanking processes to remove non-image pixels from the histogram calculation function, as distinguished from fixed-pixel histogram calculation known in the prior art.

In particular, a mask comprising the shape and position of the collimator is used to determine whether or not a pixel is to be included in the histogram calculation at the time the histogram is calculated. The position within the background processing chain where the histogram calculation occurs is shifted with respect to known techniques. The mask is calculated based on the known or specified size and shape of the physical collimator, and the distance between the X-ray source and flat panel X-ray detector. The histogram function uses the mask information, and background information to identify pixels to be excluded. The histogram is thereafter used in the remaining background processes or functions, including without limitation window level setting calculations and mixing for anatomical background processing.

In accordance with an embodiment of the present invention, not only are the physical pixels specified by the mask excluded from the image and excluded from histogram calculation (corresponding to the pixels under the physical collimator), but background pixels are preferably excluded from the histogram calculation as well. It should be noted that certain regulatory agencies that control medical device use and manufacture require that displayed images include an area representing image portions that derive from collimation, and that are distinguishable from the ROI and simple background in the displayed image, e.g., live image.

Figure 3:
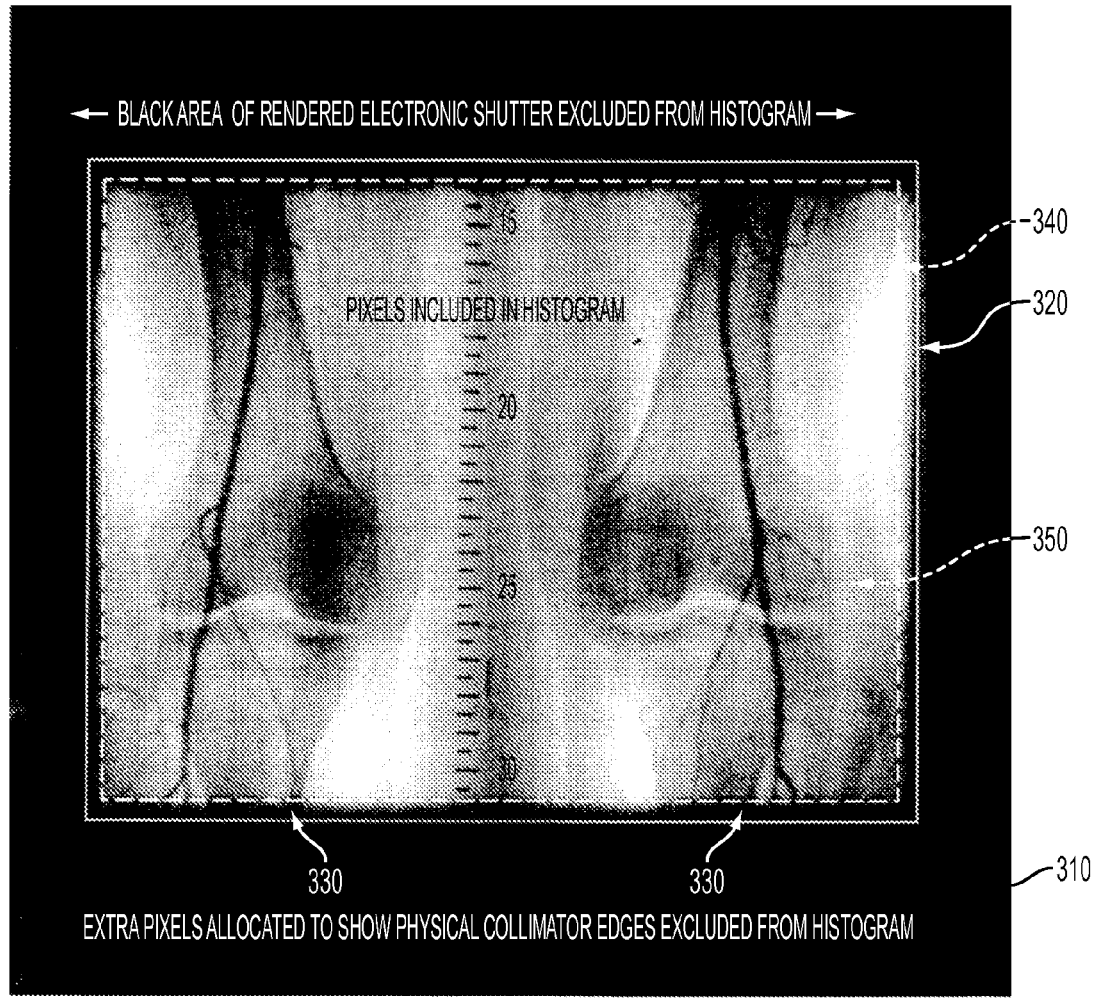
FIG. 3 is an exemplary live X-ray image, including designations that clearly identify a border portion representative of collimator mask and background in the live X-ray image.

FIG. 3 depicts an X-ray image 300 of a lower portion of a patient's legs taken during an angiographic procedure using system 2 of FIG. 1. X-ray image 300 shows image pixels that are included in the histogram and histogram calculation, and those pixels shown in the image but not included in the histogram. That is, a first black image border area 310 indicates the image area of the rendered electronic shutter comprising pixels that are excluded from the histogram calculation. A first white border 320 is included in the figure separating the electronic shutter defined from a second black border area 330 within which those pixels acquired under the collimator mask are located. First white border 320 is not included in actual displayed images during normal operation. The second black border area 330 may be included in the displayed image to comply with regulatory requirements. The second border area 330 is separated from the displayed ROI image 350, by a second white border 340. As with the first white border, the second white border is displayed only in the drawing figure for explanation purposes, and not displayed during actual imaging applications. What is particularly important for purposes of the invention is that the first and second black borders 310 and 330, while included in the displayed image 300, are excluded from the histogram calculation. Again, doing so realizes images with improved window viewing and improved contrast.

Figure 4:
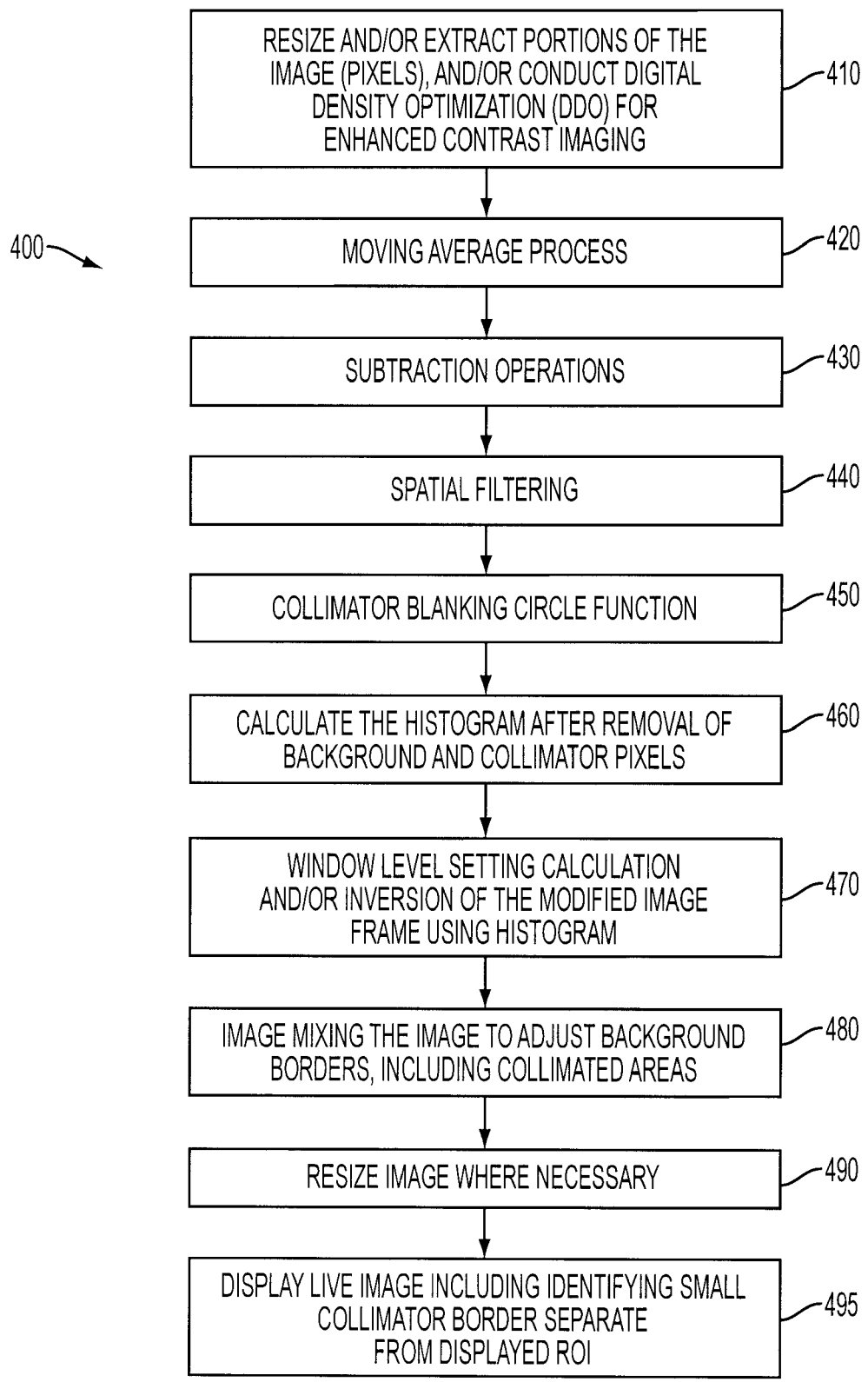
FIG. 4 is a schematic block diagram of an imaging chain of the X-ray diagnostic imaging system within with improved histogram calculation in accordance with an embodiment of the invention.

FIG. 4 is a schematic block diagram of an imaging chain of the X-ray diagnostic imaging system 2, within which the improved exemplary histogram calculations are carried out. The imaging chain 400 functions to calculate an exemplary histogram in a system processor such as that included in the image control and processing system 6 of inventive system 2. It should be noted, however, that control of inventive imaging chain or background processing may be implemented in any known X-ray system. An image control and processing means or sub-system receives the acquired latent image data in digital form from detector 8, designated in the figure as a first imaging chain function 410. Function 410 resizes and/or extracts portions of the image, and may apply digital density optimization (DDO) for enhanced contrast imaging, or otherwise manipulate the primary latent image frame data for intended future preprocessing operations. The resized image data may be stored in a primary storage output, and provided to a moving average process, as represented by block 420. That is, functional block 420 calculates a moving average or low pass temporal filtering operation on the image frame data, per pixel.

The filtered image frame data may then be processed to carry out subtraction operations, when required, in functional block 430. In such case, a mask frame input is shifted by an amount provided by vertical integer pixel shift information (as known to the skilled artisan), and the shifted mask is subtracted from the pre-processed latent or raw image frame.

The subtraction result is filtered in a spatial filter, represented by block 440. The modified frame is then provided to a collimator blanking circle function, as indicated by block 450, which identifies background and collimator masked pixels in the image frame. Image frame or ROI data with the background and collimator pixels removed is used to calculate the histogram in block 460. A mask containing the shape and position of the collimator is generated based on the known size and shape of the physical collimator, and collimator positioning at the time the image frame is taken. For background, the pixel removal includes using the known distance between the X-ray source, beam-limiting blades (shutter) and detector. The mask is utilized to determine whether a pixel, or pixel portion, is to be included in the histogram calculation function. That is, the pixels used to calculate the histogram are not predetermined as in the prior art. In addition to the pixels specified by mask, additional pixels may be excluded from the histogram to comply with known safety requirements.

Window level calculation and inversion of the modified image frame is conducted in the function represented by block 470, wherein the improved histogram is utilized to calculate the window levels. The function represented by block 480 may use the histogram and calculated window level settings to mix the image to make the adjustments in the ROI background to highlight the anatomy in the ROI, including adding at least one of a first and second border in a manner related to the description above. The image frames are resized where necessary in the function represented by block 490, and depending on the monitor, the gray scales may be converted (e.g., from 12 bits to 8 bits). The image is displayed as represented by block 495, and may be formatted for PACS storage, VCR format, etc., and output.

Figure 5:
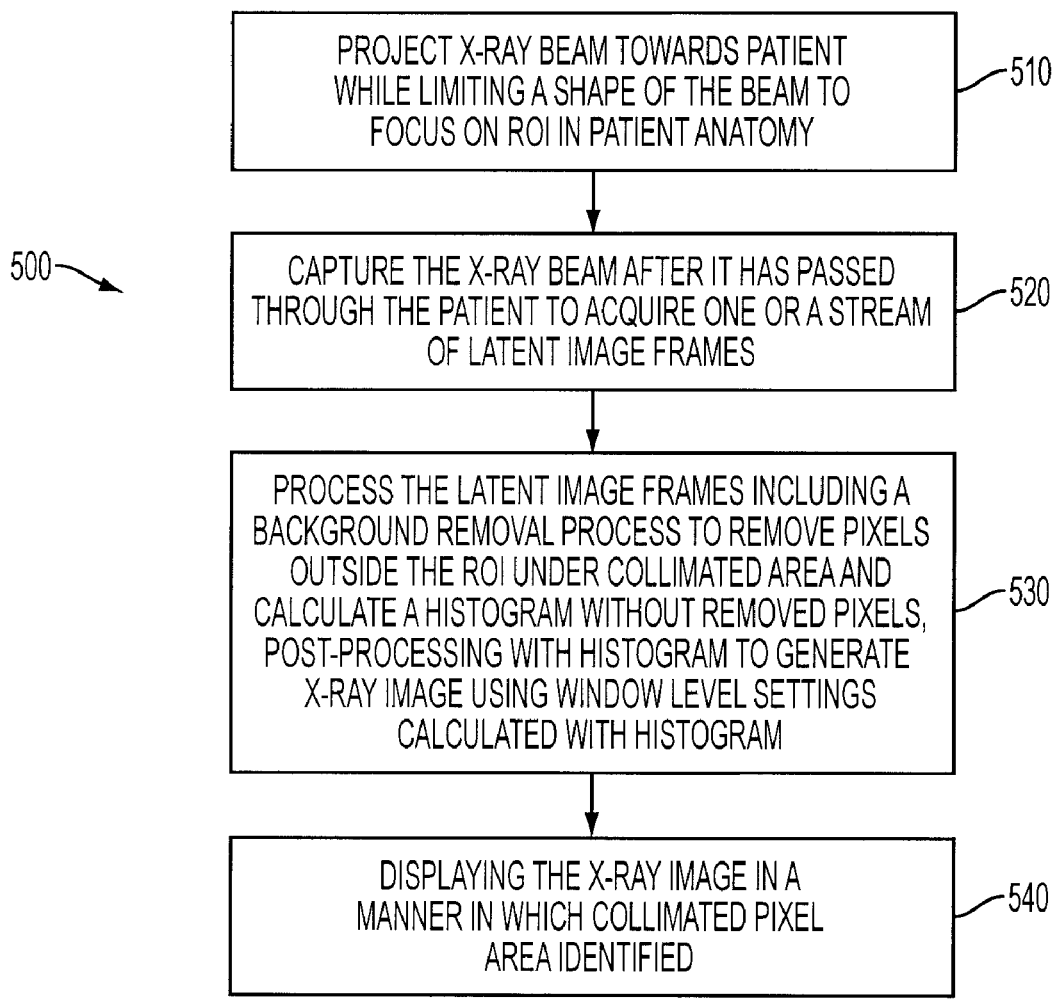
FIG. 5 is a schematic flow diagram that depicts an embodiment of the method for X-ray imaging including improved histogram calculation.

FIG. 5 depicts a preferred method 500 for X-ray imaging and implementing the improved histogram calculation in accordance with an embodiment of the invention. Block 510 represents a step of projecting an X-ray beam towards a patient under examination, including limiting a shape of the X-ray beam to focus imaging upon a region of interest (ROI) within the patient's anatomy. Block 520 represents a step of capturing the X-ray beam after it has passed through the patient to acquire one or a stream of latent image frames. Block 530 represents a step of processing the latent image frames including implementing a background removal process to remove pixels that fall outside the ROI, and calculating a histogram for the image without the removed pixels. The histogram is used in post-step processing, for example, for calculating window level settings and rendering a live X-ray for display. The displayed image includes the contrast-adjusted ROI and an image boarder designating the collimated area, and preferably a background border surrounding the displayed collimated image area. Block 540 represents a step of displaying the live X-ray image.

Although a few examples of the present invention have been shown and described, it would be appreciated by those skilled in the art that changes may be made in these embodiments without departing from the principles and spirit of the invention, the scope of which is defined in the claims and their equivalents.

The invention claimed is:

1. An X-ray diagnostic imaging system, comprising:
an X-ray source for generating and controlling an X-ray beam radiated towards a patient under examination, the X-ray source comprising an X-ray tube and X-ray collimator assembly;
an X-ray imaging device arranged for receiving the X-ray beam after it has passed through the patient and acquiring latent image frames of a region of interest (ROI) of the patient's anatomy;
a system controller coupled to the X-ray source and X-ray imaging device for controlling latent image frame acquisition and post-acquisition processing, including controlling X-ray tube, X-ray collimator assembly and X-ray imaging device positioning;
an image processing chain comprising an image processor that is coupled to the system controller, which receives the latent image frames from the X-ray imaging device for processing, including calculating a histogram for use in various image processing functions, the calculation being carried out by excluding use of collimator pixels and by excluding use of displayed pixels comprising a border region of a ROI lying within the collimated area in which X-rays are attenuated by a collimator; and
a display device coupled to the image processing chain for displaying a post-processed image frame as an X-ray diagnostic image of the ROI including said pixels comprising said border region within the collimated area in which X-rays are attenuated by a collimator.

2. The X-ray diagnostic imaging system as set forth in claim 1, further comprising a user interface coupled to the system controller which enables a user to input control signals to control latent image frame acquisition and post-acquisition processing.

3. The X-ray diagnostic imaging system as set forth in claim 1, wherein the image processing chain uses the histogram to determine an image in a series of images that shows the most contrast.

4. The X-ray diagnostic imaging system as set forth in claim 2, constructed for carrying out live X-ray fluoroscopy.

5. The X-ray diagnostic imaging system as set forth in claim 4, constructed for carrying out live X-ray fluoroscopic roadmapping.

6. The X-ray diagnostic imaging system as set forth in claim 1, further comprising a user workstation.

7. The X-ray diagnostic imaging system as set forth in claim 1, further comprising a hard disk or other direct memory device for storing the X-ray diagnostic images.

8. The X-ray diagnostic imaging system as set forth in claim 1, wherein the histogram is used to calculate automatic window level settings.

9. The X-ray diagnostic imaging system as set forth in claim 8, wherein the X-ray diagnostic image is arranged in DICOM format.

10. The X-ray diagnostic imaging system as set forth in claim 1, further comprising an image contrast injector and contrast injector control mechanism coupled to the system controller and controllable via a user interface.

11. The X-ray diagnostic imaging system as set forth in claim 2, wherein the user interface comprises at least one of a keyboard, a trackball device, a joystick, a mouse, a touch pad, a light pen, and an eye sensor.

12. The X-ray diagnostic imaging system as set forth in claim 1, further comprising a patient-support table with table control means in electrical communication with the system controller, wherein the X-ray source is mounted above the table such that a user may control table and patient position via a user interface to affect FOV.

13. The X-ray diagnostic imaging system as set forth in claim 1, further comprising a patient-support table with table control means in electrical communication with the system controller, wherein the X-ray source is mounted below the table such that a user may control table and patient position via a user interface to affect FOV.

14. The X-ray diagnostic imaging system as set forth in claim 1, further comprising a console in communication with the X-ray system, which console includes a display and user interface by which a user may conduct imaging operations at a fixed distance from the system.

15. The X-ray diagnostic imaging system as set forth in claim 1, wherein the image processing chain forms the X-ray diagnostic image for display to include said border region proximate the ROI and readily distinguishable from the ROI that is representative of the collimated area.

16. The X-ray diagnostic imaging system as set forth in claim 15, wherein said border region is identified specifically in the displayed image as deriving from a collimated area.

17. The X-ray diagnostic imaging system as set forth in claim 16, wherein the image processing chain forms the X-ray diagnostic image for display to indicate a second border bordering said border region and is indicative of the background removed from the imaged FOV.

18. The X-ray diagnostic imaging system as set forth in claim 17, wherein said border and said second border are separately identified in a displayed image.

19. A method for X-ray diagnostic imaging, comprising the activities of:
   generating and controlling an X-ray beam radiated towards a patient under examination, the X-ray source comprising an X-ray tube and X-ray collimator assembly;
   receiving the X-ray beam after it has passed through the patient and acquiring latent image frames of a region of interest (ROI) of the patient's anatomy;
   controlling latent image frame acquisition and post-acquisition processing, including controlling X-ray tube, X-ray collimator assembly and X-ray imaging device positioning;
   receiving the latent image frames for processing, including calculating a histogram for use in various image processing functions by excluding use of collimator pixels and by excluding use of displayed pixels comprising a border region of a ROI lying within the collimated area in which X-rays are attenuated by a collimator; and
   a display device coupled to the image processing chain for displaying a post-processed image frame as an X-ray diagnostic image of the ROI including said pixels comprising said border region within the collimated area in which X-rays are attenuated by a collimator.

* * * * *